(12) United States Patent
Granzotto

(10) Patent No.: US 6,244,376 B1
(45) Date of Patent: Jun. 12, 2001

(54) STETHOSCOPE HEAD

(76) Inventor: Artemio Granzotto, Hardturmstrasse 135 CH-8005, Zürich (CH)

( * ) Notice: Subject to any disclaimer, the term of this patent is extended or adjusted under 35 U.S.C. 154(b) by 0 days.

(21) Appl. No.: 09/423,846

(22) PCT Filed: Apr. 16, 1998

(86) PCT No.: PCT/CH98/00142
§ 371 Date: Nov. 15, 1999
§ 102(e) Date: Nov. 15, 1999

(87) PCT Pub. No.: WO98/51221
PCT Pub. Date: Nov. 19, 1998

(30) Foreign Application Priority Data

May 13, 1997 (CH) ................................................. 1115/97

(51) Int. Cl.[7] .................................................... A61B 7/02
(52) U.S. Cl. ........................................... 181/131; 181/137
(58) Field of Search ................................. 181/131, 137; 381/67

(56) References Cited

U.S. PATENT DOCUMENTS 4,440,258   4/1984   Packard .
4,995,473   2/1991   Packard .
5,883,339 * 3/1999   Greenberger ......................... 181/131

FOREIGN PATENT DOCUMENTS 0 119 870 B1   9/1984   (EP) .
0 179 971     10/1984   (EP) .
0 500 279 B1   8/1992   (EP) .

* cited by examiner

Primary Examiner—Khanh Dang
(74) Attorney, Agent, or Firm—Pauley Petersen Kinne & Fejer

(57) ABSTRACT

A stethoscope head for a one-way stethoscope with a membrane. The stethoscope has a funnel or bell-shaped resonance body. A membrane and the resonance body enclose a resonance chamber that is interconnected to the air column in the lumen of a tube. A capsule of a soundproof material completely surrounds a distal region of the resonance body without contact, leaving just an opening through which the tube passes. A suspension element of elastomer material forms a mobile connection between the capsule and the holding ring attached to the peripheral rim of the resonance body.

20 Claims, 2 Drawing Sheets

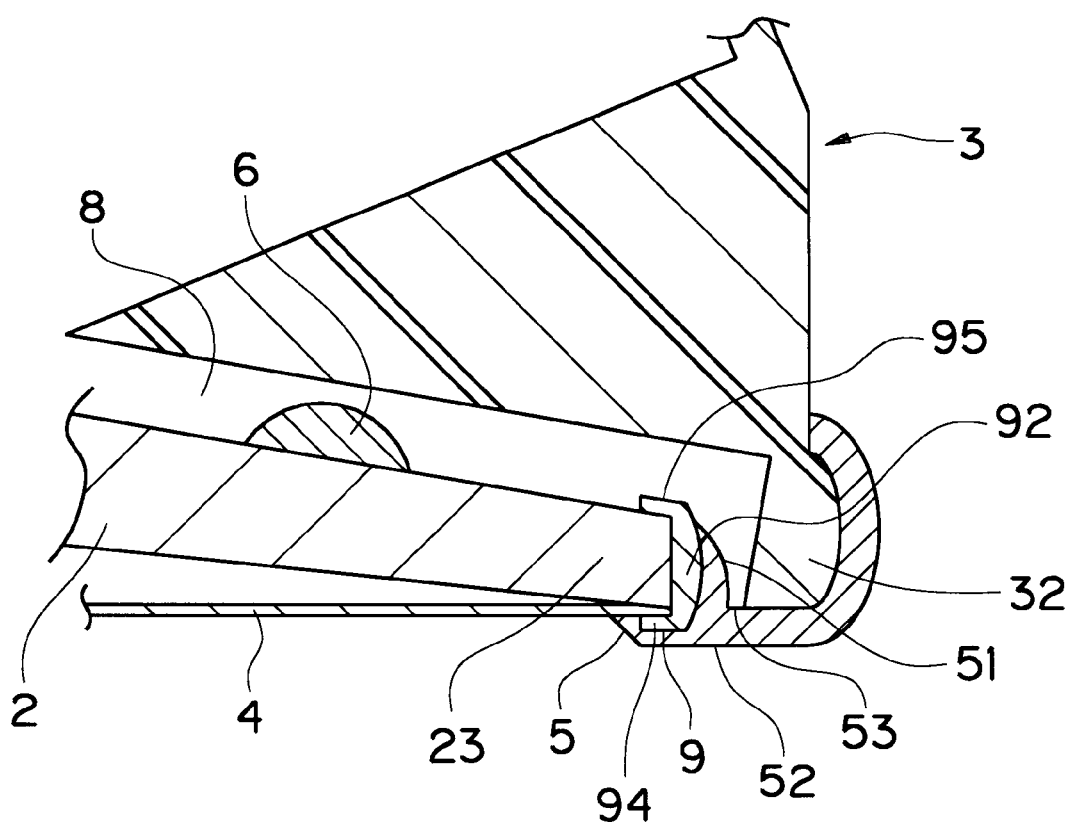

STETHOSCOPE HEAD

BACKGROUND OF THE INVENTION

1. Field of the Invention

This invention relates to a stethoscope head for a one-way stethoscope.

2. Description of Prior Art

Although the stethoscope was introduced by T. R. H. Laennec, the founder of auscultation, almost 180 years ago, the mechanical-acoustic stethoscope still represents one of the most important and most often employed diagnostic tools in the daily practice of physicians. The diagnostic auscultation of organs, primarily the heart and the lungs, for sound phenomena provide an experienced physician with a wealth of acoustic information regarding the state of health of the patient.

The originally employed open listening tubes were replaced by the currently used stethoscopes, which has a headpiece or chest piece, with a hose system with bow-equipped ear pieces or headsets for transmitting sound to the ear. The headpieces have bell-shaped resonance bodies for receiving the body sound, which can be opened or covered by a diaphragm. Although the open resonance bodies are well suited for detecting low-frequency sound, they must be pressed tightly against the surface of a body of a patient, since the skin of the patient must close, tightly positioned with respect to the lower rim of the resonance body over its entire circumference in order to assure a satisfactory function. If the system is not closed, sound can escape to the outside, sound energy is lost and the efficiency of the stethoscope is reduced. The strong pressure of the resonance body can cause the patient pain and the skin of the patient is arched by the strong pressure and penetrates more or less deeply into the bell body. The free resonance space is reduced by this, and the resonance body must accordingly be designed relatively tall in order to prevent it from being completely filled with skin.

In connection with diaphragm-equipped resonance bodies, the sound-conducting system of the chest piece is normally closed. Therefore the headpiece does not need to be pressed on at all or only slightly during auscultation, and the rigid diaphragm rests on the skin of the patient. Since the skin and the diaphragm resting on it do not arch at all, or only slightly, the resonance body can be designed to be relatively flat. However, the rigidity of the diaphragm muffles low-frequency sounds.

To combine the advantages of both systems, two-way or even multi-way stethoscopes were developed, which have an open and a closed resonance funnel in a headpiece or even several headpieces for different frequency ranges.

Different stethoscope heads were developed for employing the advantages of diaphragm-equipped systems and for detecting low frequencies at the same time.

A two-way stethoscope head with a diaphragm which is floatingly seated is described in European Patent Reference EP-A-0 119 870. The diaphragm is loosely seated between an underside of the resonance body and the lower circumferential rim of a retaining ring fastened on the resonance body. Thus, the diaphragm can be moved up and down over a short distance, which is slightly less than its height. By varying the contact pressure, the diaphragm and the resonance body are intended to selectively form an open or a closed acoustic system and accordingly to make auscultation of low-frequency or high-frequency body sounds possible.

A stethoscope headpiece is described in U.S. Pat. No. 4,440,258, with a diaphragm that can be moved in the vertical direction between two relative positions with respect to the resonance body, wherein the acoustic rigidity of the diaphragm is changed and the stethoscope can be tuned to different frequency levels.

An adapter made of an elastomeric material for a stethoscope head is described in U.S. Pat. No. 4,995,473, which encloses the basic range of the stethoscope head. The hollow-cylindrical adapter tapers toward the side facing the patient. If the stethoscope head having the adapter is placed on the body surface of the patient, the air space between the body surface and the diaphragm is sealed in a soundproof manner against the outside without the diaphragm coming into contact with the body surface.

An ergonometric breast piece of a stethoscope is known from European Patent Reference EP-A-0 500 279. A raised centerpiece with two lateral recessed grips is placed on the resonance body to ease grasping and holding of the stethoscope head and to simultaneously make possible the operation of control elements, which are attached to the centerpiece for controlling the volume.

Great demands are made on the stethoscope and also on the examining physician in the course of detecting and evaluating the acoustic signals. To be able to make optimal use of the acoustic information and therefore to prevent wrong diagnoses, a great deal of experience on the part of the physician is required and the signal provided by the stethoscope must be of high quality, reproducible and as free as possible of external interference signals.

To facilitate and aid the diagnosis, it has been attempted for some time to acoustically amplify the noise emanating from the body using microphones and amplifiers. The use of microcomputers and custom-made diagnostic software in phonocardiography is a further step in making the interpretation of the sound phenomena easier. The increasing miniaturization of electronic and computer components provides for such systems, which are integrated into handy devices, in the ideal case in a slightly enlarged stethoscope head.

Whether the direct sound is evaluated in the customary manner, or a signal transformed with computer assistance into electrical voltage changes, the quality of the received information is decisively dependent on the acoustic signal primarily received on the surface of the body. This primary signal is negatively affected by various factors. Noise from the surroundings is received and passed on by the resonance body. Noises, which are generated on a body surface of a patient in the form of substrate noises caused by holding the resonance body or by applying the resonance body, or by parts which are in unmuffled contact with the resonance body, generate distracting noises and interferences. There is an additional problem because of differences in the contact pressure of the stethoscope on the body surfaces, the reproducibility of the auscultated signals is not always assured.

The signals emanating from the physician are transmitted through his or her hand to the stethoscope head and result in interfering overlaid extraneous signals.

SUMMARY OF THE INVENTION

It is one object of this invention to provide a stethoscope head which does not have the disadvantages mentioned.

This object is attained by a device in accordance with the features described in this specification and in the claims.

BRIEF DESCRIPTION OF THE DRAWINGS

An exemplary embodiment of this invention is represented in the drawings and explained in the following description wherein:

FIG. 3 shows an enlargement of a detail of a cross section along the median plane taken through a peripheral area of a further embodiment of the stethoscope head.

DESCRIPTION OF PREFERRED EMBODIMENTS

Figure 1:
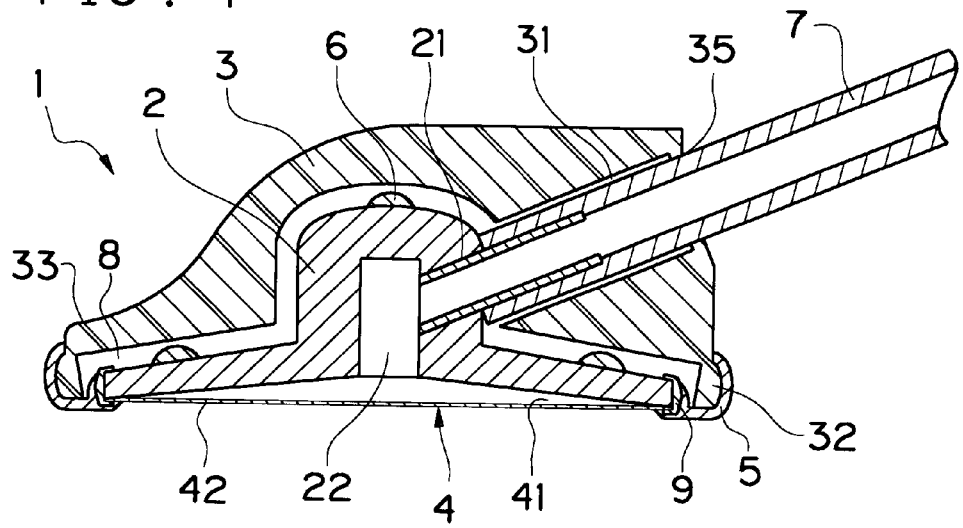
FIG. 1 shows a cross section taken through a stethoscope head along a median plane.
Figure 2:
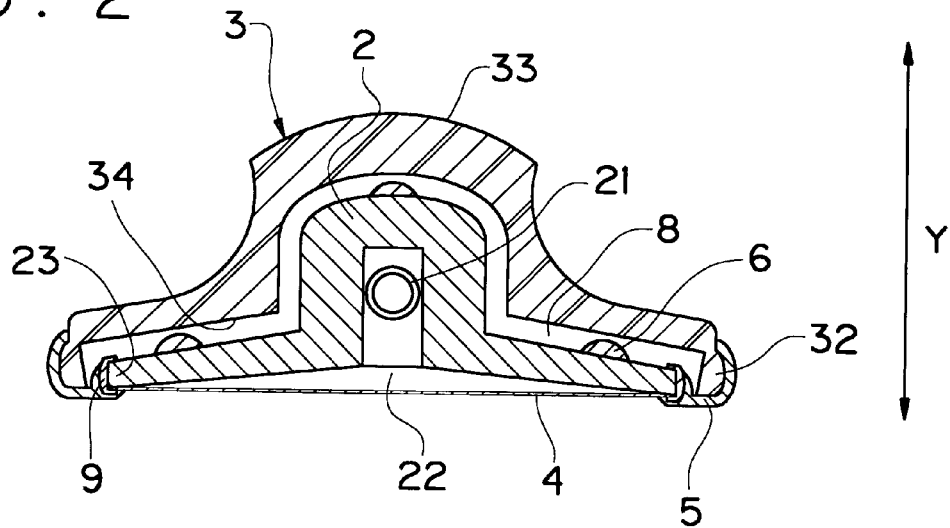
FIG. 2 shows a cross section taken through the stethoscope head along the frontal plane.

A stethoscope head 1 represented in FIGS. 1 and 2 has a bell-shaped resonance body 2 made of a suitable metal, such as aluminum, steel, iron or brass. Also known are resonance bodies made of plastic, but they are not very advantageous because of their relatively poor acoustic properties. A connector 21 is arranged on a side of the resonance body 2, on which a hose 7 made of plastic or rubber is placed. The resonance body 2 has a peripheral continuous collar 23, which has a base surface 24 on a base side which faces a body surface of a patient when used. The peripheral area of a flat, disk-shaped diaphragm 4 is clampingly held in an interlocking and frictionally connected manner between the base surface 24 and a clamping surface 91 of a holding ring 9. Since the base surface 24, a top 41 and an underside 42 of the diaphragm 4, and the clamping surface 91 are located in approximately parallel planes, and since the diaphragm 4 is clampingly maintained over 360°, equal clamping forces act all around on the diaphragm 4. A vertical cylinder 92 of the holding ring 9 has an inwardly projecting, circumferential basal or proximal holding rib 94 which supports the clamping surface 91. The holding ring 9 is screwed together with the peripheral collar 23 of the bell body 2, or is inverted over the outside of the collar 23, and is clampingly maintained on it by means of an additional distal holding rib 95.

A resonance chamber 22 is enclosed between the resonance body 2 and the diaphragm 4. The air in the resonance chamber 22 is in communication with the air column in the hose 7 via the connector 21. The side of the resonance body 2, which faces away or is distal from the body surface of the patient during an examination, is completely enclosed in a sound-insulating capsule 3 made of plastic. The capsule 3 is ergonomically shaped, so that it fits the hand of the physician, as well as possible. So that the stethoscope head can also be held as dependably as possible even with wet hands, an exterior surface 33 of the capsule 3 is textured, or the capsule 3 has an additional anti-slip coating. The capsule 3 has a lateral passage 31, through which the hose 7, which is fastened on the resonance body 2, is passed. A proximal side 34 of the capsule 3, or the side facing the resonance body 2, is shaped in such a way that a continuous gas-filled or air-filled gap 8, which is at least some millimeters wide, is created all over between the capsule 3 and the resonance body 2. The capsule 3 does not touch the resonance body 2 at any place, as long as no great pressure is exerted on it. The air gap 8 also continues along the hose 7 until close to an outlet point 35 of the hose 7 from the capsule 3. There, the hose 7 is tightly enclosed over a length of several millimeters by the insulating material of the capsule 3, so that the air gap 8 is sealed from the surrounding atmosphere in a gas-tight, or at least approximately gas-tight manner. Sealing of the capsule 3 against the hose 7 can alternatively also be provided by a separate seal of insulating material.

The capsule 3, which is made of a sound-insulating material, partially acts as a second resonance body, which amplifies a total resonance so that the auscultated sound gains in clarity and strength.

In the area of its proximal edge 32, the wall of the capsule 3 is thickened in a bead-like manner toward the exterior. A circumferential, sealing suspension 5 acts on this bead 32 and on the holding ring 9, which bridges the air gap 8 between the capsule 3 and the holding ring 9 fastened on the resonance body 2. The resonance body 2, the diaphragm 4 and the holding ring 9 form a rigid system. They are therefore movably connected together with the capsule 3 via the suspension 5. The material from which the suspension 5 is made is resilient enough to make possible a limited relative mobility of the resonance body 2 with respect to the capsule 3. The suspension 5 extends over the entire width of the base holding rib 94 of the holding ring 9 and tightly rests over its entire circumference at a width of approximately 0.5 mm against a base side 42 of the diaphragm 4. In this way the suspension 5 assures the sound insulation between the body surface of the patient and the resonance body 2 in two ways. The substrate noise between the body and the holding ring 9 and the resonance body 2 connected with it is muffled, as well as the air noise between the body surface and the air gap 8 surrounding the resonance body 2. In the area which bridges the air gap between the capsule 3 and the resonance body 2, the suspension 5 can be designed in various ways. In an advantageous embodiment of this invention, a distal surface 51 and a proximal surface 52 of the suspension 5 lie approximately parallel with each other in the area bridging the air gap between the capsule 3 and the resonance body 2, wherein the suspension in this area has a thickness between 0.1 mm and 1.0 mm, preferably 0.3 mm. The suspension 5 can also be thicker in this area and, as represented in FIG. 3, can have a level proximal surface 52 and an arched distal surface 51. If the suspension is thicker than 1.0 mm in this area, a circumferential depression or groove 53, which is U-shaped or V-shaped, is advantageously cut on the distal side 51, and the thickness of the suspension 5 is reduced at its thinnest part to 0.1 mm to 1.0 mm, advantageously 0.3 mm.

The resonance body 2, and the diaphragm 4 connected with it, can be displaced by a few millimeters and as well tilted by a few degrees in relation to the capsule 3 along the Y axis. The deflection is limited on the one side by the suspension 5 and on the other side by the inside width of the air gap 8. In order to prevent a direct contact of the resonance body 2 with the inside of the capsule 3 even under a strong deflection, vibration-reducing insulating nipples 6 made of a soft elastomeric material are attached to the distal side of the resonance body 2. The height of the nipples 6 is less than the inside width of the air gap 8 in the state of rest. Thus, if the capsule 3 is pressed against the body surface at high pressure, the counter-pressure of the latter on the diaphragm-supporting presses the insulation nipples 6 against the inside of the capsule 3. The soft, resilient nipples 6 can absorb a portion of the effect of the energy by deformation, but with increasing pressure pass on more pressure to the resonance body 2. If the examining physician desires, he therefore can disable the resilient suspension of the stethoscope head by stronger pressure on the capsule 3, and to press down the diaphragm 4 with any desired force. But the noise insulation between the capsule 3 and the resonance body 2 is assured in every case.

Tests have shown that the qualitatively best auscultation results are obtained by means of high-quality stethoscopes while maintaining a steady low contact or placement pressure. The pressure, with which the diaphragm 4 rests on the body surface, is ideally determined by the weight of the resonance body 2 itself, which is normally in the range of 60 to 70 grams. However, such low contact pressures are very difficult to generate and control manually. With the stethoscope head 1 of this invention, the examining physician can press the encapsulated stethoscope head 1 at various pressures against the body surface of the patient without the pressure on the diaphragm 4 being essentially changed, because resilient seating permits a yielding of the diaphragm-supporting system. Thus, the entire unit comprising the diaphragm 4, the holding ring 9 and the resonance body 2 is displaced toward the capsule by the pressure on the diaphragm 4 and the areas of the suspension 5 located underneath the holding ring 9. With a conventional diaphragm, which is rigidly seated on the stethoscope head 1, a stronger pressure on the stethoscope head 1 results in a more or less uneven arching and in unevenly distributed pressure forces over the entire area of the diaphragm 4. But since the suspension 5 in accordance with this invention permits a vertical yielding and lateral tilting of the diaphragm 3 and the entire diaphragm-supporting system to a limited degree in relation to the capsule 3 held by the examining physician, the diaphragm 4 can rest on the body surface while maintaining its shape, wherein a relatively homogeneous pressure distribution over the entire surface of the diaphragm 4 is achieved. This improves the acoustic properties of the stethoscope head 1.

In addition, the suspension 5, which closes tightly against the capsule 3 and also tightly against the base side of the diaphragm 4, constitutes an effective barrier against fluids and solids. It prevents them from penetrating the air gap 8 and therefore prevents the contamination and soiling of inner areas of the capsule 3 and of the resonance body 2. Because of the encapsulation in accordance with this invention, the stethoscope head 1 has an almost seamlessly closed surface, which makes its cleaning and disinfection very easy. Since the stethoscope is used in a hygienically sensitive area and it is necessary to reduce the risk of transmitting pathogenes, this has a decisive advantage. With respect to the material from which the suspension 5 is shaped this means that it must also well withstand aggressive and abrasive disinfectants and disinfecting methods.

In a further advantageous embodiment of this invention, the suspension 5 and the holding ring 9 are made of one piece. This is particularly cost-effective. The pressure of the diaphragm 4 against the resonance body 2 can also be kept as low as possible in this way.

As shown in FIG. 1, no part of the stethoscope head 1 made of metal comes into direct contact with the body surface of the patient. Only the diaphragm 4 and the suspension 5 are in contact with the body of the patient. Since both are made of material with a low heat conductivity, there is no contact with cold metal, which is unpleasant to the patient when placing the stethoscope head 1 on the body surface. This cold shock can create strong reactions, in particular with babies and small children, and can make their examination extremely difficult and tedious.

Miscellaneous pre-warming of the head element 1 prior to the examination is no longer required with this invention. A device for warming the stethoscope, such as described in European Patent Reference EP-A-0 179 971, can also be omitted.

Since in the course of auscultation there is no direct contact between the metallic resonance body 2 of the stethoscope head 1 and the body surface of the patient, it is no longer necessary when selecting the metal alloys to consider their allergenic properties. The selection can be solely determined by the acoustic qualities. Hypo-allergenic materials are advantageously selected for the diaphragm 4 and the capsule 3 and the suspension 5 made of plastic.

What is claimed is:

1. In a stethoscope head (1) for a one-way stethoscope with a funnel-shaped or bell-shaped resonance body (21), which has a peripheral uninterrupted circumferential collar (23) having a base surface (24), wherein a peripheral area of a level circularly-shaped diaphragm (4) is held in an interlocking and frictionally connected manner between the base surface (24) and a clamping surface (91) of a holding ring (9), so that a resonance chamber (22) is enclosed by the diaphragm (4) and the resonance body (2), which is in communication with an air column in a passageway of a hose (7), the improvement comprising: a capsule (3) made of a noise-insulating material completely and in a contactless way surrounding a distal area of the resonance body (2), a passage (31) for the hose (7) is free and a suspension (5) of an elastomeric material forms a movable connection between the capsule (3) and the holding ring (9), fastened on the circumferential collar (23) of the resonance body (2), wherein at least one insulating nipple (6), made of an elastomeric material, is attached to a distal side of the resonance body (2) having a height less than an inside width of the air gap (8).

2. In the stethoscope head (1) in accordance with claim 1, wherein a suspension (5) is fastened on one side on a peripheral bulge (32) of the capsule (3) and on an other side on the holding ring (9), wherein the suspension (5) extends over an entire width of a basal circumferential holding rib (94) of the holding ring (9) and rests interlockingly over an entire circumference against a base side (42) of the diaphragm (4).

3. In the stethoscope head (1) in accordance with claim 2, wherein a continuous air gap (8) exists between the capsule (3) and the resonance body (2) which is closed off in a basal area by the suspension (5) between the capsule (3) and the holding ring (9) attached to the resonance body (2).

4. In the stethoscope head (1) in accordance with claim 2, wherein the suspension (5) has a thickness of between 0.1 mm and 1.0 mm in an area which bridges the air gap (8).

5. In the stethoscope head (1) in accordance with claim 2, wherein in an area which bridges the air gap (8) the suspension (5) has a circumferential depression (51), and at a thinnest point the suspension (5) has a thickness of between 0.1 mm and 1.0 mm.

6. In the stethoscope head (1) in accordance with claim 1, wherein the suspension (5) and the holding ring (9) are made of one piece.

7. In the stethoscope head (1) in accordance with claim 6, wherein the suspension (5) has a thickness of between 0.1 mm and 1.0 mm in an area which bridges the air gap (8).

8. In the stethoscope head (1) in accordance with claim 6, wherein in an area which bridges the air gap (8) the suspension (5) has a circumferential depression (51), and at a thinnest point the suspension (5) has a thickness of between 0.1 mm and 1.0 mm in this area.

9. In the stethoscope head (1) in accordance with claim 1, wherein the capsule (3) is ergonomically shaped.

10. In the stethoscope head (1) in accordance with claim 1, wherein the capsule (3) is shaped from one of a sound-insulating material and a plastic foam material.

11. In the stethoscope head (1) in accordance with claim 1, wherein the diaphragm (4) is made of one of a plastic material, a fiberglass, an epoxy resin and a thin sheet metal with a smooth base surface (42).

12. In the stethoscope head (1) in accordance with claim 1, wherein the diaphragm (4), the suspension (5) and the capsule (3) are made of hypo-allergenic materials.

13. In a stethoscope head (1) for a one-way stethoscope with a funnel-shaped or bell-shaped resonance body (21), which has a peripheral uninterrupted circumferential collar (23) having a base surface (24), wherein a peripheral area of a level circularly-shaped diaphragm (4) is held in an interlocking and frictionally connected manner between the base surface (24) and a clamping surface (91) of a holding ring (9), so that a resonance chamber (22) is enclosed by the diaphragm (4) and the resonance body (2), which is in communication with an air column in a passageway of a hose (7), the improvement comprising: a capsule (3) made of a noise-insulating material completely and in a contactless way surrounding a distal area of the resonance body (2), a passage (31) for the hose (7) is free and a suspension (5) of an elastomeric material forms a movable connection between the capsule (3) and the holding ring (9), fastened on the circumferential collar (23) of the resonance body (2), wherein a suspension (5) is fastened on one side on a peripheral bulge (32) of the capsule (3) and on an other side on the holding ring (9), wherein the suspension (5) extends over an entire width of a basal circumferential holding rib (94) of the holding ring (9) and rests interlockingly over an entire circumference against a base side (42) of the diaphragm (4).

14. In the stethoscope head (1) in accordance with claim 13, wherein at least one insulating nipple (6), made of an elastomeric material, is attached to a distal side of the resonance body (2) having a height less than an inside width of the air gap (8).

15. In the stethoscope head (1) in accordance with claim 13, wherein a continuous air gap (8) exists between the capsule (3) and the resonance body (2) which is closed off in a basal area by the suspension (5) between the capsule (3) and the holding ring (9) attached to the resonance body (2).

16. In the stethoscope head (1) in accordance with claim 13, wherein the suspension (5) and the holding ring (9) are made of one piece.

17. In the stethoscope head (1) in accordance with claim 13, wherein the capsule (3) is ergonomically shaped.

18. In the stethoscope head (1) in accordance with claim 13, wherein the capsule (3) is shaped from one of a sound-insulating material and a plastic foam material.

19. In the stethoscope head (1) in accordance with claim 13, wherein the suspension (5) has a thickness of between 0.1 mm and 1.0 mm in an area which bridges the air gap (8).

20. In the stethoscope head (1) in accordance with claim 13, wherein in an area which bridges the air gap (8) the suspension (5) has a circumferential depression (51), and at a thinnest point the suspension (5) has a thickness of between 0.1 mm and 1.0 mm in this area.

* * * * *